US009746536B2

(12) United States Patent
Wang et al.

(10) Patent No.: US 9,746,536 B2
(45) Date of Patent: Aug. 29, 2017

(54) INTERLEAVED BLACK AND BRIGHT BLOOD IMAGING FOR INTERLEAVED DYNAMIC CONTRAST ENHANCED MAGNETIC RESONANCE IMAGING

(71) Applicants: KONINKLIJKE PHILIPS N.V., Eindhoven (NL); UNIVERSITY OF WASHINGTON, Seattle, WA (US)

(72) Inventors: Jinnan Wang, Seattle, WA (US); Huijun Chen, Seattle, WA (US); Peter Boernert, Hamburg (DE); Chun Yuan, Belluvue, WA (US)

(73) Assignees: Koninklijke Philips N.V., Eindhoven (NL); University of Washington, Seattle, WA (US)

( * ) Notice: Subject to any disclaimer, the term of this patent is extended or adjusted under 35 U.S.C. 154(b) by 117 days.

(21) Appl. No.: 14/651,851

(22) PCT Filed: Dec. 12, 2013

(86) PCT No.: PCT/IB2013/060831
§ 371 (c)(1),
(2) Date: Jun. 12, 2015

(87) PCT Pub. No.: WO2014/091433
PCT Pub. Date: Jun. 19, 2014

(65) Prior Publication Data
US 2015/0323636 A1 Nov. 12, 2015

Related U.S. Application Data

(60) Provisional application No. 61/737,194, filed on Dec. 14, 2012.

(51) Int. Cl.
*G01R 33/563* (2006.01)
*A61B 5/026* (2006.01)
*G01R 33/56* (2006.01)

(52) U.S. Cl.
CPC ........ *G01R 33/5635* (2013.01); *A61B 5/0263* (2013.01); *G01R 33/5607* (2013.01); *G01R 33/56366* (2013.01); *G01R 33/5601* (2013.01)

(58) Field of Classification Search
CPC ............ G01R 33/5607; G01R 33/5635; A61B 5/0263
See application file for complete search history.

(56) References Cited

U.S. PATENT DOCUMENTS

| 6,552,542 B1 | 4/2003 | Overall |
| 7,369,887 B2 | 5/2008 | Fayad et al. |

(Continued)

FOREIGN PATENT DOCUMENTS

| CN | 101185571 A | 5/2008 |
| EP | 2309286 A1 | 4/2011 |

(Continued)

OTHER PUBLICATIONS

Tan, EK T. et al "Fast Inversion Recovery Magnetic Resonance Angiography of the Intracranial Arteries", Magnetic Resonance in Medicine, vol. 63, No. 6, 2010, pp. 1648-1656.

(Continued)

*Primary Examiner* — Joseph M Santos Rodriguez

(57) ABSTRACT

A magnetic resonance system (10), and corresponding method, image a subject using a conversion-free interleaved black and bright blood imaging (cfIBBI) sequence. A MR scanner (12) is controlled to perform a plurality of repetitions of a black blood imaging sequence (52). The black blood imaging sequence (52) includes a tissue nulling sub-sequence followed by a black blood acquisition sub-sequence (56) performed a time interval (TI) after the tissue nulling sub-sequence. The MR scanner (12) is further controlled to, between successive repetitions of the black blood imaging sequence (52), perform a bright blood imaging sequence (54) including the tissue nulling sub-sequence followed by a bright blood acquisition sub-sequence (58) performed the time interval (TI) after the tissue nulling sub-sequence. The time intervals (TI) of the black blood imaging sequence (52) and the bright blood imaging sequence (54) are of the same duration.

16 Claims, 3 Drawing Sheets

(56) References Cited

U.S. PATENT DOCUMENTS

| 8,076,934 B2 | 12/2011 | Herzka et al. |
| 2011/0181283 A1 | 7/2011 | Grinstead |

FOREIGN PATENT DOCUMENTS

| JP | 2002143125 A | 5/2002 |
| WO | 2012143824 A1 | 10/2012 |

OTHER PUBLICATIONS

Fan, Zhaoyang et al "Time-Resolved Contrast-Enhanced Black-Blood Carotid Vessel Wall Imaging with SRDIR", Proceedings of the International Society for Magnetic Resonance in Medicine, vol. 20, 2012, pp. 3822.

Wu, Tingting et al "Conversion-free Interleaved Black Blood and Bright Blood Imaging (cfIBBI) Sequence for Dynamic Contrast Enhanced (DCE) MRI of Vessel Wall", Proceedings of the International Society for Magnetic Resonance in Medicine, vol. 21, 2013, pp. 1310.

Fan, Zhaoyang et al "Black-Blood Dynamic Contrast-Enhanced Coronary Artery Wall MRI: A Potential Tool for Kinetic-Modeling-based Wall Inflammation Assessment", Proceedings of the International Society for Magnetic Resonance in Medicine, vol. 21, 2013, pp. 0876.

Wang, J. et al "Interleaved Local Excited Black Blood (LOBBI) and Bright Blood MRI for Improved Vessel Wall DCE", Proceedings of the International Society for Magnetic Resonance in Medicine, vol. 19, 2011, pp. 1234.

Kerwin, William et al "Quantitative Magnetic Resonance Imaging Analysis of Neovasculature Volume in Carotid Atherosclerotic Plaque", Circulation, vol. 107, No. 6, 2003, pp. 851-856.

Yarnykh, Vasily L. et al "T1-Insensitive Flow Suppression using Quadruple Inversion-Recovery", Magnetic Resonance in Medicine, vol. 48, No. 5, 2002, Abstract.

INTERLEAVED BLACK AND BRIGHT
BLOOD IMAGING FOR INTERLEAVED
DYNAMIC CONTRAST ENHANCED
MAGNETIC RESONANCE IMAGING

CROSS-REFERENCE TO PRIOR APPLICATIONS

This application is the U.S. National Phase application under 35 U.S.C. §371 of International Application No. PCT/IB2013/060831, filed on Dec. 12, 2013, which claims the benefit of U.S. Provisional Patent Application No. 61/737,194, filed on Dec. 14, 2012. These applications are hereby incorporated by reference herein.

The following relates generally to medical imaging. It finds particular application in conjunction with interleaved black and bright blood imaging and will be described with particular reference thereto. However, it is to be understood that it also finds application in other usage scenarios and is not necessarily limited to the aforementioned application.

Interleaved black and bright blood imaging (IBBI) is useful for dynamic contrast enhanced (DCE) vessel wall magnetic resonance imaging (MRI) since it allows for simultaneous acquisition of both high spatial resolution images of the vessel wall (the black blood images) and high temporal resolution images (the bright blood images) for determining the arterial input function (AIF). Current implementations of IBBI DCE, however, are typically limited in that they usually require post acquisition processing before the signals from black and bright blood images can be directly compared. This requires extra data acquisition and extra processing time. Further, the conversion can introduce error.

The following provides new and improved methods and systems which overcome the above-referenced problems and others.

In accordance with one aspect, a magnetic resonance (MR) system for imaging a subject is provided. The system includes an electronic data processing device configured to control a MR scanner. The MR scanner is controlled to perform a plurality of repetitions of a black blood imaging sequence. The black blood imaging sequence includes a tissue nulling sub-sequence followed by a black blood acquisition sub-sequence performed a time interval after the tissue nulling sub-sequence. The MR scanner is further controlled to, between successive repetitions of the black blood imaging sequence, perform a bright blood imaging sequence including the tissue nulling sub-sequence followed by a bright blood acquisition sub-sequence performed the time interval after the tissue nulling sub-sequence. The time intervals of the black blood imaging sequence and the bright blood imaging sequence are of the same duration.

In accordance with another aspect, a magnetic resonance (MR) method for imaging a subject is provided. The method includes performing a plurality of repetitions of a black blood imaging sequence using an MR scanner. The black blood imaging sequence includes about a 90 degree radiofrequency (RF) pulse, a black blood acquisition sub-sequence for black blood imaging, and a delay spanning from the 90 degree RF pulse of the black blood imaging sequence to the black blood acquisition sub-sequence. The method further includes, between successive repetitions of the black blood imaging sequence, performing a bright blood imaging sequence using the MR scanner, the bright blood imaging sequence including about a 90 degree RF pulse, a bright blood acquisition sub-sequence for bright blood imaging, and said delay spanning from the 90 degree RF pulse of the bright blood imaging sequence to the bright blood acquisition sub-sequence. The delays of the black blood imaging sequence and the bright blood imaging sequence are of the same duration.

In accordance with another aspect, a magnetic resonance (MR) system for imaging a subject is provided. The system includes an MR scanner configured to perform a plurality of repetitions of a black blood imaging sequence. The black blood imaging sequence includes a tissue signal nulling sub-sequence with a radiofrequency (RF) pulse, an acquisition sequence for black blood imaging, and a delay spanning from the RF pulse of the tissue nulling sub-sequence of the black blood imaging sequence to the acquisition sequence of the black blood imaging sequence. The MR scanner is further configured to perform a plurality of repetitions of a bright blood imaging sequence interleaved with the plurality of repetitions of the black blood imaging sequence. The bright blood imaging sequence includes the tissue signal nulling sub-sequence with the RF pulse, an acquisition sequence for bright blood imaging, and a delay spanning from the RF pulse of the tissue nulling sub-sequence of the bright blood imaging sequence to the acquisition sequence of the bright blood imaging sequence. The delays of the black blood imaging sequence and the bright blood imaging sequence are of the same duration.

One advantage resides in generating black and bright blood images with directly comparable signals.

Another advantage resides in black and bright blood signals with the same tissue contrasts.

Another advantage resides in removing signal interference between black and bright blood images.

Another advantage resides in robust blood suppression during black blood imaging.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

It is recognized herein that the inability to directly compare black blood and bright blood images acquired by interleaved black and bright blood imaging (IBBI) is due to the different contrast mechanisms typically used to generate the black and bright blood images. For example, using motion sensitized driven equilibrium (MSDE) for black blood imaging and time-of-flight (TOF) for bright blood imaging precludes direct comparison of the signals obtained for black imaging and bright blood imaging. Thus, the signal behaviors for these different contrast mechanisms are governed by different rules.

Additional challenges with current implementations of IBBI include removal of signal interferences between black and bright blood images and robust blood suppression during black blood imaging. Black blood preparation should not alter the blood signals in the bright blood images and vice versa. Further, the blood suppression should be consistent between both pre- and post-injection of contrast agents.

Disclosed herein is an improved pulse sequence for IBBI, referred to herein as conversion-free IBBI (cfIBBI), that generates directly comparable signals for black and bright blood images. The disclosed cfIBBI technique also provides robust blood suppression after contrast injection during black blood imaging.

Figure 1:
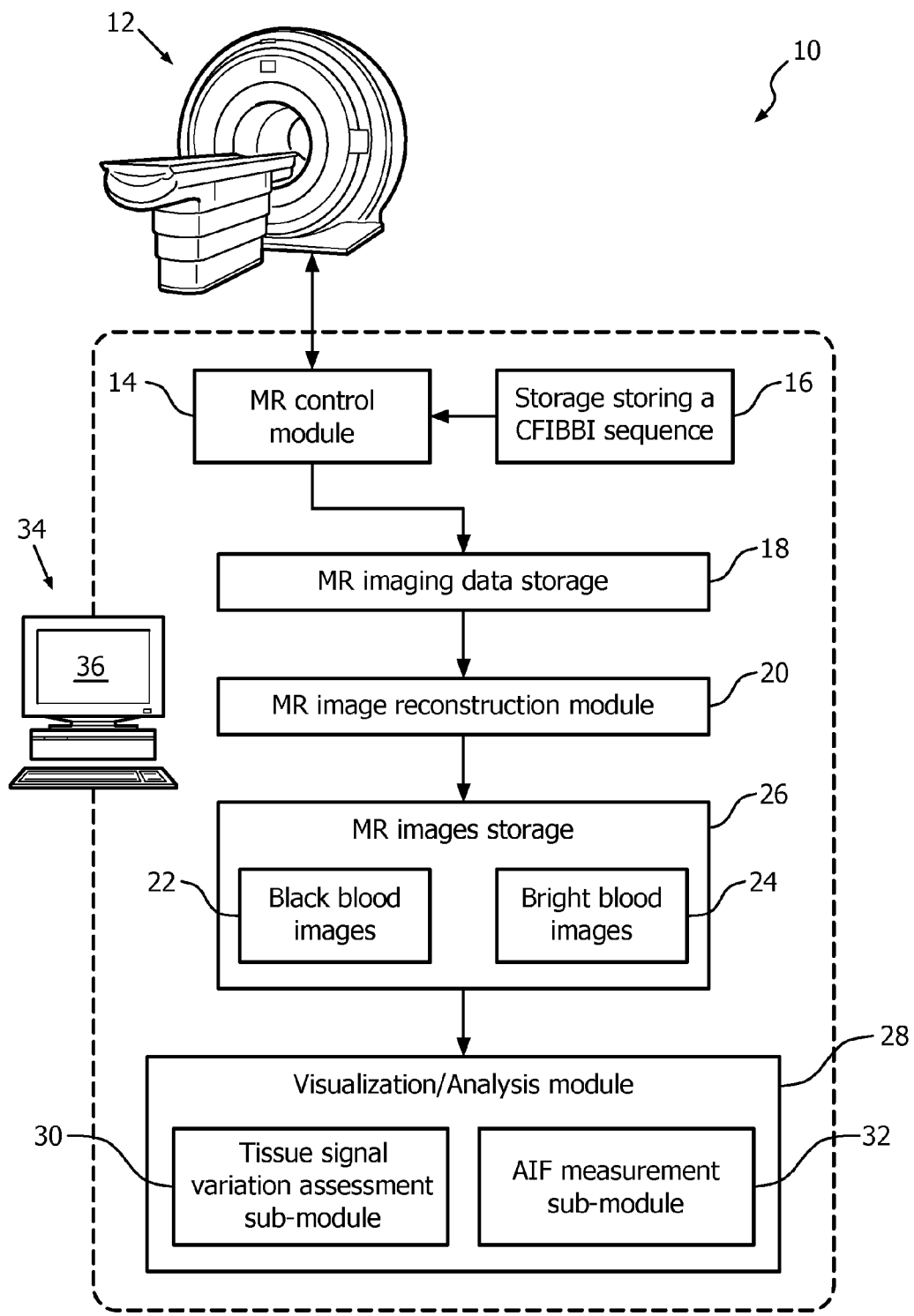
FIG. 1 illustrates a magnetic resonance angiography (MRA) system employing conversion-free interleaved black and bright blood imaging (cfIBBI).

With reference to FIG. 1, an illustrative magnetic resonance angiography (MRA) system 10 is described, which employs a cfIBBI pulse sequence. The MRA system 10 includes an magnetic resonance (MR) scanner 12 operated by a MR control module 14 to retrieve from a sequences storage 16 a cfIBBI sequence, and to execute the retrieved cfIBBI sequence to perform imaging of a subject (for example, a human subject, a veterinary subject, a clinical or pre-clinical test subject, or so forth). The MR scanner 12 can be any type of commercial or non-commercial magnetic resonance imaging (MRI) scanner, such as (by way or illustrative example) an Achieva™, Ingenia™, Intera™, or Panorama™ MRI scanner (available from Koninklijke Philips Electronics N.V., Eindhoven, The Netherlands).

The performed cfIBBI sequence generates MR imaging data for black and bright blood sequence modules if the cfIBBI sequence that are suitably stored in an MR imaging data storage 18. Typically, the cfIBBI sequence generates MR imaging data for four bright blood images for every one black blood image, although other ratios are contemplated. In that regard, the spatial resolution of black blood images are typically higher than the spatial resolution of bright blood images, and the temporal resolution of bright blood images are typically higher than black blood images.

An MR image reconstruction module 20 applies a suitable image reconstruction algorithm to the MR imaging data generated by the black blood sequence module (which may, for example, use a MSDE black blood imaging technique) to generate one or more MR images 22 having black blood contrast (that is, one or more black blood MRA images 20). The reconstruction module 20 also applies a suitable image reconstruction algorithm to the MR imaging data generated by the bright blood sequence module (which may, for example, use a TOF bright blood imaging technique, or may employ an exogenous contrast agent injected into the bloodstream) to generate one or more MR images 24 having bright blood contrast (that is, one or more bright blood MRA images 24). The black and bright blood images 22, 24 are suitably stored in an MR images storage 26. The choice of image reconstruction algorithm depends upon the spatial encoding employed in the imaging data acquisition and may, for example, be a Fourier transform-based image reconstruction algorithm.

An image visualization/analysis module 28 performs display and/or analysis of the black and bright blood images 22, 24. In an illustrative application, inflammatory features of atherosclerotic plaque are quantified to evaluate inflammation in early lesion and the fibrous cap region (for plaque rupture). Toward this end, a tissue signal variation assessment sub-module 30 processes the black blood images 22 to assess or quantify tissue signal variations in a region proximate to the lumen, while an arterial input function (AIF) measurement sub-module 32 processes the bright blood images 24 to assess or quantify the AIF. Typically, black blood images provide more accurate lumen definition compared with TOF based bright blood images because TOF may be affected by blood velocity reduction proximate to blood vessel walls. On the other hand, bright blood images contain information for computing AIF.

The data processing and control components 14, 20, 28, 30, 32 are suitably implemented by an electronic data processing device 34, such as a suitably programmed illustrative computer 34, a network based server, or so forth, that includes or has operative access to a display device 36 via which the visualization module 28 displays images and/or image analysis results. In some embodiments, analog or mixed circuitry may also be included (e.g., parallel reconstruction pipeline hardware optionally used in the image reconstruction module 20). The MR control module 14 is optionally implemented as a separate dedicated MR control computer. The image visualization module 28 may be implemented as a dedicated image processing workstation with a high resolution display.

The instrument control and data processing aspects of the disclosed MRA imaging techniques employing cfIBBI can also be embodied as a non-transitory storage medium (not shown), such as a hard disk or other magnetic storage medium, optical disk or other optical storage medium, random access memory (RAM), flash memory or other electronic storage medium, or so forth, which stores instructions that are executable by the electronic data processing device 34 to perform the disclosed techniques.

Figure 2A:
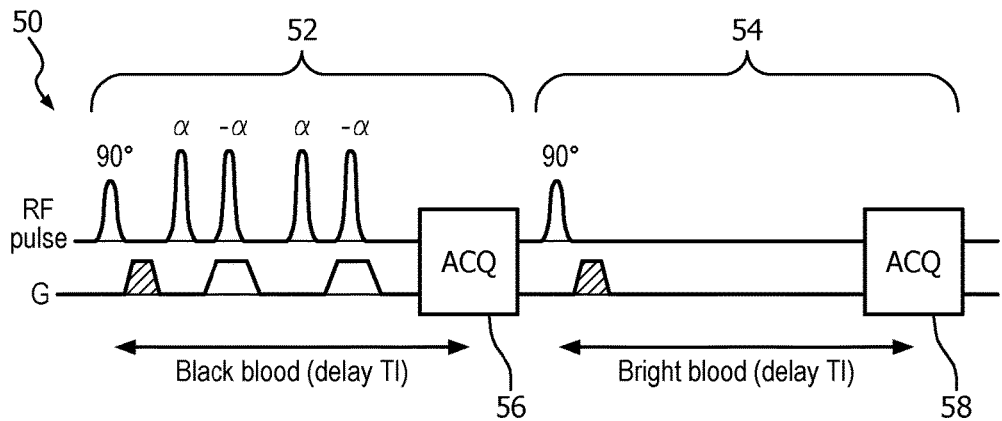
FIG. 2A illustrates one embodiment of a cfTBBI pulse sequence.
Figure 2B:
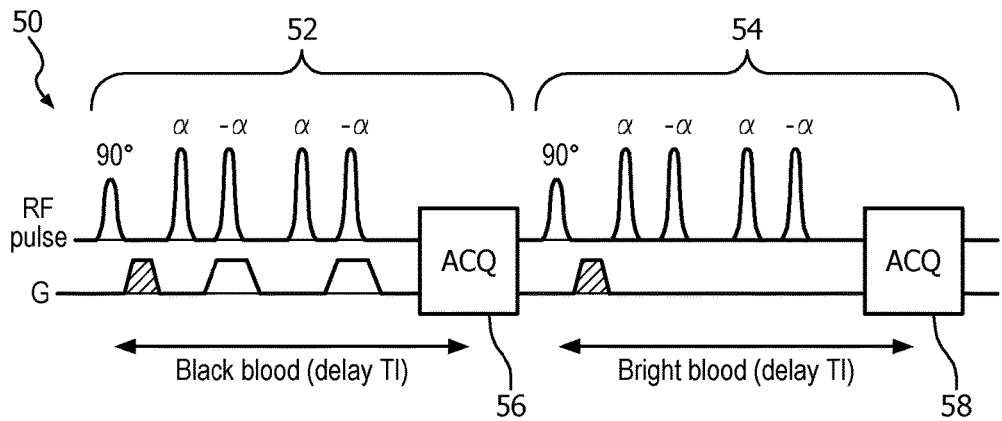
FIG. 2B illustrates another embodiment of a cfTBBI pulse sequence.

With reference to FIGS. 2A and 2B, pulse diagrams illustrating two embodiments of a cfIBBI pulse sequence 50 are shown. In each of FIGS. 2A and 2B, the top plot labeled "RF pulse" diagrammatically shows applied radio frequency (RF) pulses, and the bottom plot labeled "G" diagrammatically shows applied magnetic field gradients. The abscissa of both plots is time. The cfIBBI pulse sequence includes a black blood imaging module 52 and a bright blood imaging module 54 corresponding to the first and second halves, respectively, of the pulse diagrams. The black blood imaging module 52 and the bright blood imaging module 54 can each be repeated n times in an interleaved fashion, where n≥1. For example, the black blood imaging module 52 is typically executed immediately subsequent to and/or immediately prior to execution of the bright blood imaging module 54.

The black and bright blood imaging modules 52, 54 each include an acquisition module or sub-sequence 56, 58. The acquisition module or sub-sequence 56, 58 includes a sequence of pulses and magnetic field gradients to generate MR signals for image reconstruction. For example, the acquisition module 58 for bright blood imaging can use a gradient echo sequence, as well as other types of T1 weighted (for AIF measurement) techniques, such as spin echo (SE) or echo planar imaging (EPI). As another example, the acquisition module 56 for black blood imaging can use Spin Echo (SE) techniques in which the outflow effect is used to suppress the blood signal or motion sensitized driven equilibrium (MSDE) techniques. The acquisition module 56, 58 for a black or bright blood image is chosen based on the specific use case. However, the acquisition modules 56, 58 for black and bright blood imaging should be same to make the MR signals comparable.

In an illustrative example in which the cfIBBI sequence generates MR imaging data for four bright blood images for every one black blood image, a single instance of the bright blood imaging module 54 suitably generates a complete data set for a single bright blood image, while four instances of the black blood imaging module 52 generate a complete data set for single black blood image. Alternatively, two instances of the bright blood imaging module 54 may be used to generate a complete data set for a single bright blood image while eight instances of the black blood imaging module 52 may be used to generate a complete data set for a single black blood image, or so forth.

Further, each of the black and bright blood imaging modules 52, 54 includes a spatially non-selective RF pulse of about 90 degrees (i.e., 90 degrees +/−5 degrees) followed by a spoiler gradient field to null the tissue signal. Further, the spoiler gradient field immediately follows the 90 degree RF pulse. In FIGS. 2A and 2B, this spoiler gradient field is highlighted by shading. The 90 degree RF pulse precedes the acquisition module 56, 58 and a delay (i.e., an inversion time TI) is interposed. The inversion time delay TI for black and bright blood imaging is the same. In this way, the tissue signals are expected to be the same at the time of acquisition for both black blood and bright blood imaging. As a result, the blood signals obtained from the AIF can be directly modeled with the tissue signals obtained from black blood images. The 90 degree pulse can also remove signal interferences between the black and bright blood imaging modules 52, 54 by nulling all tissue signals at the beginning of each imaging modules. While a 90 degree pulse is illustrated, other flip angles are contemplated, with the flip angle and inversion time (TI) chosen to provide the desired tissue nulling.

Figure 3A:
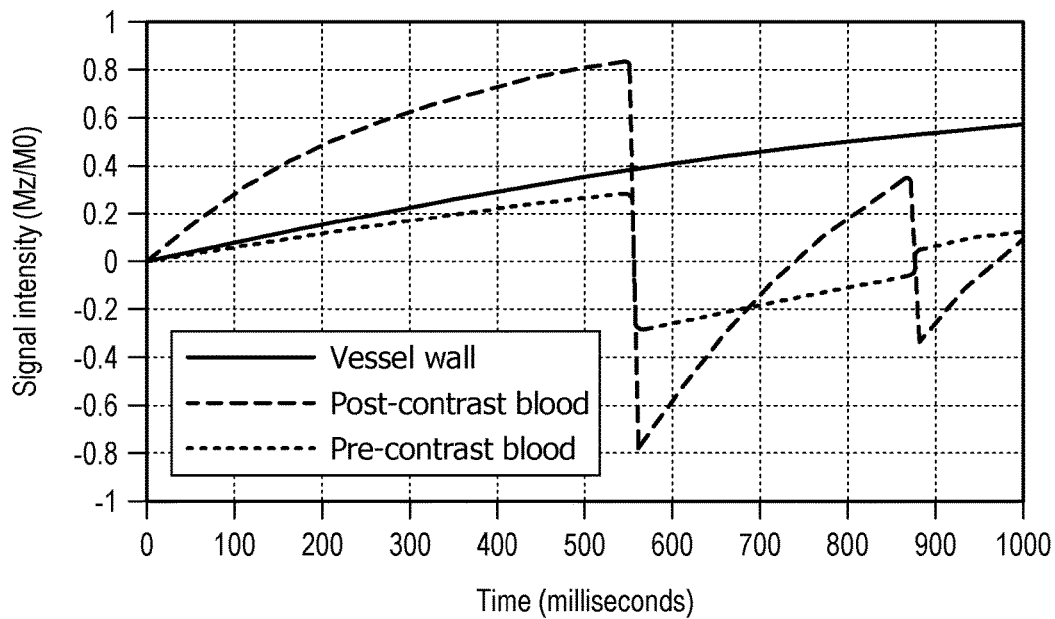
FIG. 3A illustrates a simulated plot of vessel wall, pre-contrast blood, and post-contrast blood signals for a black blood imaging module.
Figure 3B:
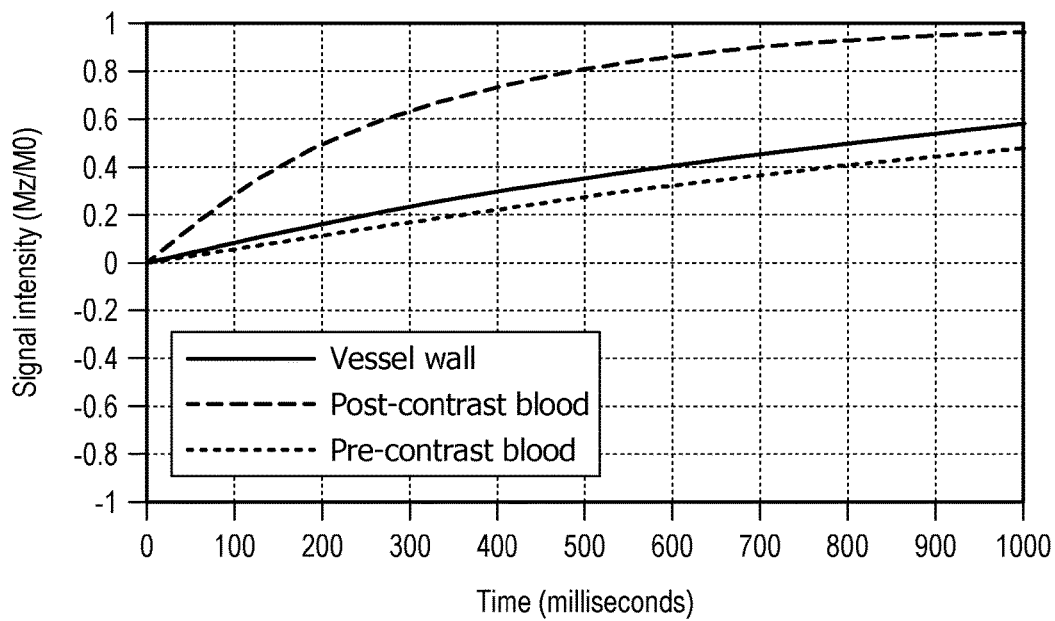
FIG. 3B illustrates a simulated plot of vessel wall, pre-contrast blood, and post-contrast blood signals for a bright blood imaging module.

With reference to FIGS. 3A and 3B, simulated plots include tissue signals for black blood imaging (FIG. 3A) and for bright blood imaging (FIG. 3B), respectively, as a function of time after the tissue signal null. The vertical axis corresponds to signal intensity (i.e., Mz/M0) and the horizontal axis corresponds to time. The plots of FIGS. 3A and 3B simulate vessel wall signals (solid lines), pre-contrast blood signals (dotted lines), and post-contrast blood signals (dashed lines) for black blood and bright blood imaging modules 52, 54, respectively. As can be seen, both plots include the same vessel wall (i.e., tissue) signal, rising from the null condition to Mz/M0~0.59 over a 1000 msec interval.

With returning reference to FIGS. 2A and 2B, in the illustrative black blood imaging module 52, two consecutive pairs of $\alpha/-\alpha$ RF pulses are interposed between the 90 degree RF pulse and the acquisition module 56 during the inversion time delay TI to manipulate the blood signal. Each pair includes a spatially non-selective $\alpha$ RF pulse and a spatially selective $-\alpha$ RF pulse, the $-\alpha$ RF pulse following the $\alpha$ RF pulse and including a spatial selection magnetic field gradient such that the tissue signal is flipped back to equilibrium by the pulse pair while the blood signal is flipped.

The magnitude of a may be about 180 degrees (i.e., 180 degrees +/−5 degrees), but can vary depending upon the imaging application from 0 degrees to 359 degrees. For example, $\alpha$ could be 120 degrees. Using two pairs of $\alpha/-\alpha$ RF pulses can remove the T1 sensitivity of the blood nulling effect. The plots of FIGS. 3A and 3B are simulated for $\alpha$=180 degrees. When $\alpha$ is 180 degrees, it follows that $\alpha=-\alpha$ and the $\alpha/-\alpha$ sub-sequence corresponds to the 180 degree pulses of a Quadruple Inversion-Recovery (QIR) sequence (see, e.g., Yarnykh et al, "$T_1$-Insensitive Flow Suppression Using Quadruple Inversion-Recovery", Magnetic Resonance in Medicine vol. 48 pages 899-905 (2002)). QIR is known for its universal blood suppression independent of the blood T1 values post contrast injection. This TI insensitivity can be seen in the simulated tissue signals of FIGS. 3A and 3B. It is recognized herein that when $\alpha$ is other than 180 degrees (e.g., less than 180 degrees), a shorter inversion time TI can be used to achieve blood nulling in the black blood imaging module 52. For IBBI, this can advantageously reduce imaging time and help improve the imaging acquisition efficiency. A shorter inversion time TI can also help maintain the approximate linear relationship between exogenous contrast agent concentration and MR signal intensity.

In the cfIBBI sequence shown in FIG. 2A, the bright blood imaging module 54 does not include $\alpha$ and $-\alpha$ RF pulses interposed between the 90 degree RF pulse and the acquisition module 58. However, in some embodiments, the bright blood imaging module 54 include two consecutive pairs of $\alpha/-\alpha$ RF pulses interposed between the acquisition module 58 and the 90 degree RF pulse during the inversion time TI to manipulate the blood signal, as illustrated in FIG. 2B. The two consecutive pairs of $\alpha/-\alpha$ RF pulses are as described above, except that the $-\alpha$ RF are not selective (i.e., do not include a field gradient). By employing consecutive pairs of $\alpha/-\alpha$ RF pulses in both the black blood imaging module 52 and the bright blood imaging module 54, the tissue signals are better comparable. It is also contemplated to repeat the $\alpha/-\alpha$ sequence more than twice during the inversion time delay TI, or alternatively to include only a single $\alpha/-\alpha$ sequence in the inversion time delay TI.

The cfIBBI sequence advantageously provides interleaved black blood and bright blood dynamic contrast enhanced (DCE) imaging with a high spatial resolution. In this type of imaging, the cfIBBI sequence provides comparable signal intensities between the two imaging modules, so that the AIF, tissue signal and other signals can all be directly used for DCE pharmaco kinetic analysis and/or modeling. Applications include, for example, carotid, aortic, cardiac, peripheral, whole-body plaque DCE imaging. Moreover, while interleaved black blood and bright blood imaging is described as an illustrative example with numerous clinical applications, the disclosed approach can be generalized to interleaved black fluid and bright fluid imaging of other types of fluid boundary layers.

With returning reference to FIG. 1, the resulting black and bright blood images can be variously processed to generate useful clinical information. For example, the images can be used in DCE kinetic modeling (see, e.g., Kerwin et al, "Quantitative Magnetic Resonance Imaging Analysis of Neovasculature Volume in Carotid Atherosclerotic Plaque", Circulation, 2003 Feb. 18, 107(6):851-6, incorporated herein by reference in its entirety). DCE kinetic modeling with cfIBBI advantageously allows smaller structures to be visualized and disease to be diagnosed earlier.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A magnetic resonance system for imaging a subject, said system comprising:
   an electronic data processing device configured to control a MR scanner to:
   perform a plurality of repetitions of a black blood imaging sequence, the black blood imaging sequence including a tissue nulling sub sequence followed by a black blood acquisition sub sequence performed a time interval after the tissue nulling sub sequence;
   between successive repetitions of the black blood imaging sequence, perform a bright blood imaging sequence including the tissue nulling sub sequence followed by a bright blood acquisition sub sequence performed the time interval after the tissue nulling sub sequence; wherein the time intervals of the black blood imaging sequence and the bright blood imaging sequence are of the same duration;

reconstruct MR imaging data generated by performing the black blood imaging sequence to generate a black blood image; and reconstruct MR imaging data generated by performing the bright blood imaging sequence to generate a bright blood image;

wherein the black blood imaging sequence further includes one or more consecutive pairs of RF pulses interposed between the tissue nulling sub sequence and the black blood acquisition sub sequence during the time interval, and wherein the bright blood imaging sequence includes one or more consecutive pairs of RF pulses interposed between the tissue nulling sub sequence and the bright blood acquisition sub sequence during the time interval.

2. The MR system according to claim 1, wherein the tissue nulling sub sequence comprises a spatially non selected 90 degree RF pulse followed by a spoiler field gradient.

3. The MR system according to claim 1, wherein each of the consecutive pairs of RF pulses includes an RF pulse of amplitude a followed by an RF pulse of amplitude $-\alpha$.

4. The MR system according to claim 3, wherein $\alpha$ is 180 degrees.

5. The MR system according to claim 3, wherein the RF pulse of amplitude a is spatially non selective and the RF pulse of amplitude $-\alpha$ is spatially selective.

6. The MR system according to claim 1, wherein the electronic data processing device is further configured to:
compute an arterial input function based on the bright blood image.

7. The MR system according to claim 6, further including:
a display device configured to display at least one of the black blood image, the bright blood image, and the arterial input function.

8. The MR system according to claim 1, further including:
a display device configured to display at least one of the black blood and the bright blood images.

9. A magnetic resonance (MR) method for imaging a subject, the method comprising:

performing a plurality of repetitions of a black blood imaging sequence using an MR scanner, the black blood imaging sequence including about a 90 degree radiofrequency (RF) pulse, a black blood acquisition sub sequence for black blood imaging, and a delay spanning from the 90 degree RF pulse of the black blood imaging sequence to the black blood acquisition sub sequence; and between successive repetitions of the black blood imaging sequence, performing a bright blood imaging sequence using the MR scanner, the bright blood imaging sequence including about a 90 degree RF pulse, a bright blood acquisition sub sequence for bright blood imaging, and said delay spanning from the 90 degree RF pulse of the bright blood imaging sequence to the bright blood acquisition sub-sequence;

reconstructing MR imaging data generated by performing the black blood imaging sequence to generate a black blood image; and reconstructing MR imaging data generated by performing the bright blood imaging sequence to generate a bright blood image;

wherein the delays of the black blood imaging sequence and the bright blood imaging sequence are of the same duration, wherein the black blood imaging sequence includes one or more consecutive pairs of RF pulses interposed between the about 90 degree RF pulse of the black blood imaging sequence and the black blood acquisition sub-sequence during the delay of the black blood imaging sub-sequence, and wherein the bright blood imaging sequence includes one or more consecutive pairs of RF pulses interposed between the about 90 degree RF pulse of the bright blood imaging sub-sequence and the acquisition module of the bright blood imaging sequence during the delay of the bright blood imaging sub-sequence.

10. The MR method according to claim 9, wherein the black blood imaging sequence includes a tissue nulling sub sequence comprising said about 90 degree RF pulse of the black blood imaging sequence followed by a spoiler gradient, and the bright blood imaging sequence includes the same tissue nulling sub sequence comprising said about 90 degree RF pulse of the bright blood imaging sequence followed by a spoiler gradient.

11. The MR method according to claim 10, wherein each of the consecutive pairs of RF pulses includes a $\alpha$ RF pulse and a $-\alpha$ RF pulse, $\alpha$ being within the range of 0 degrees to 359 degrees.

12. The MR method according to claim 11, wherein the a RF pulse is spatially nonselective and the $-\alpha$ RF pulse is accompanied by a spatially selective magnetic field gradient.

13. The method according to claim 9, further including:
displaying at least one of the black blood image and the bright blood image on a display device.

14. A non-transitory storage medium storing instructions executable by an electronic data processor device operating in conjunction with an MR scanner controlled by the electronic data processing device to perform a method of magnetic resonance imaging of a subject, said method comprising:

performing a plurality of repetitions of a black blood imaging sequence using an MR scanner, the black blood imaging sequence including about a 90 degree radiofrequency (RF) pulse, a black blood acquisition sub sequence for black blood imaging, and a delay spanning from the 90 degree RF pulse of the black blood imaging sequence to the black blood acquisition sub sequence; and between successive repetitions of the black blood imaging sequence, performing a bright blood imaging sequence using the MR scanner, the bright blood imaging sequence including about a 90 degree RF pulse, a bright blood acquisition sub sequence for bright blood imaging, and said delay spanning from the 90 degree RF pulse of the bright blood imaging sequence to the bright blood acquisition sub-sequence;

wherein the delays of the black blood imaging sequence and the bright blood imaging sequence are of the same duration, wherein the black blood imaging sequence includes one or more consecutive pairs of RF pulses interposed between the about 90 degree RF pulse of the black blood imaging sequence and the black blood acquisition module during the delay of the black blood imaging sequence, and wherein the bright blood imaging sequence includes one or more consecutive pairs of RF pulses interposed between the about 90 degree RF pulse of the bright blood imaging sequence and the acquisition module of the bright blood imaging sequence during the delay of the bright blood imaging sequence.

15. A magnetic resonance system for imaging a subject, said system comprising:

an MR scanner configured to:

perform a plurality of repetitions of a black blood imaging sequence, the black blood imaging sequence including a tissue signal nulling sub sequence with a radiofrequency (RF) pulse, an acquisition sub-sequence for generating black blood imaging data, and a delay spanning from the RF pulse of the tissue nulling sub sequence of the black blood imaging sequence to the acquisition sub-sequence of the black blood imaging sequence, the black blood imaging sequence further including one or more consecutive pairs of RF pulses interposed between the tissue nulling sub sequence and the acquisition sub sequence during the delay;

perform a plurality of repetitions of a bright blood imaging sequence interleaved with the plurality of repetitions of the black blood imaging sequence to generate bright blood MR imaging data, the bright blood imaging sequence including a tissue signal nulling sub sequence with an RF pulse, an acquisition sub-sequence for acquiring the bright blood imaging data, and a delay spanning from the RF pulse of the tissue nulling sub sequence of the bright blood imaging sequence to the acquisition sequence of the bright blood imaging sub-sequence, the bright blood imaging sequence further including one or more consecutive pairs of RF pulses interposed between the tissue nulling sub-sequence and the bright blood acquisition sub-sequence during the delay;

wherein the delays of the black blood imaging sequence and the bright blood imaging sequence are of the same duration, reconstruct the black blood MR imaging data generated by performing the black blood imaging sequence to generate a black blood image; and reconstruct the bright blood MR imaging data generated by performing the bright blood imaging sequence to generate a bright blood image.

16. The MR system according to claim 15, further including:

a display device configured to display at least one of the black blood image and the bright blood image.

* * * * *